(12) United States Patent
Yang et al.

(10) Patent No.: US 9,308,203 B2
(45) Date of Patent: Apr. 12, 2016

(54) PRESSURE SENSITIVE ADHESIVE MATRIX DEVICE OR SYSTEM FOR THE TREATMENT OR PREVENTION OF ONYCHOMYCOSIS OR TINEA PEDIS

(75) Inventors: Kuo-Hua Yang, Taoyuan (TW); Yung-Jin Lee, Taoyuan (TW); Li-Chin Lin, Taoyuan (TW)

(73) Assignee: TAIWAN BIOTECH CO., LTD., Taoyuan (TW)

( * ) Notice: Subject to any disclaimer, the term of this patent is extended or adjusted under 35 U.S.C. 154(b) by 628 days.

(21) Appl. No.: 12/570,656

(22) Filed: Sep. 30, 2009

(65) Prior Publication Data

US 2010/0081669 A1    Apr. 1, 2010

Related U.S. Application Data

(60) Provisional application No. 61/101,913, filed on Oct. 1, 2008.

(51) Int. Cl.
*A61K 9/70* (2006.01)
*A61K 47/14* (2006.01)
*A61K 31/496* (2006.01)

(52) U.S. Cl.
CPC .............. *A61K 31/496* (2013.01); *A61K 9/7061* (2013.01); *A61K 9/7023* (2013.01); *A61K 47/14* (2013.01)

(58) Field of Classification Search
CPC .................................................... A61K 9/7084
See application file for complete search history.

(56) References Cited

U.S. PATENT DOCUMENTS 6,585,963 B1    7/2003  Quan et al.
6,727,401 B1    4/2004  Venkateshwaran et al.

FOREIGN PATENT DOCUMENTS

CA            1192496      *  8/1985  ............... A61K 7/48

OTHER PUBLICATIONS

Small et al. (Journal of Clinical Oncology 2004, 22, 1025-1033).*
Fungal Nail Infection. Section: Preventing Fungal Nail Infectons. Patient.co.uk 2009.*
Fungal nail infection. PubMed Health. 2010.*
Fungal Nail Infections—Treatment Overview. Section: Recurring infections and prevention WebMD 2010.*
Martinez-Rossi Mycopathologia 2008, 166, 369-383.*

* cited by examiner

*Primary Examiner* — Abigail Fisher
*Assistant Examiner* — Jessica Kassa
(74) *Attorney, Agent, or Firm* — WPAT, P.C.; Anthony King

(57) ABSTRACT

Disclosed is a pressure-sensitive adhesive matrix patch device for treatment or prevention of fungal toenails or fingernails or foot infections comprising an antifungal agent or two or more antifungals in combination and adhesively secured to a dorsal site of an infected palm or foot, rather than an area of infection and surrounding skin. A method for the transdermal treatment or prevention of fungal toenails or fingernails or foot infections with an antifungal agent is also disclosed, the method comprising adhesively securing to a dorsal site of an infected palm or foot a pressure-sensitive adhesive matrix patch device for a time sufficient to deliver an effective amount of the antifungal agent to an area of infection.

12 Claims, 2 Drawing Sheets

PRESSURE SENSITIVE ADHESIVE MATRIX DEVICE OR SYSTEM FOR THE TREATMENT OR PREVENTION OF ONYCHOMYCOSIS OR TINEA PEDIS

FIELD OF THE INVENTION

The present invention relates to a device for administration of a pharmaceutical composition for treating or preventing fungal toenails or fingernails or foot infections, such as onychomycosis or tinea pedis (also called athlete's foot). Particularly, the present invention relates to a pressure-sensitive adhesive patch device comprising antifungal agents.

DESCRIPTION OF THE PRIOR ART

Tinea pedis, also called Athlete's foot, is a fungal infection of the skin that causes scaling, flaking, and itching of affected areas. Various parasitic fungi that cause tinea pedis can also cause skin infections on other areas of the body, most often under nails or around the groin. Fungal infections of the nails, referred to as "nail fungus," "onychomycosis," or "tinea unguium," are common throughout the world. An estimated, 2-13% of North Americans are affected, and at least 15-20% in the 40-60 year-old age group has one or more infected fingernails or toenails. Infections can range from superficial, causing little more than discoloration, to severe, resulting in loss of the nail together with deformities of the surrounding digit. A single antifungal drug is usually insufficient to eliminate all kinds of fungi. For instance, azole antifungal agents are effective against Candida sp., but not dermatophytes. Therefore, more than one antifungal drug is needed to effectively treat the disease.

Various systemic and topical preparations have been used to treat fungal infections. Onychomycosis is presently treated primarily with oral antifungal agents. Topical agents are rarely effective by themselves, except in some mild cases, and only affect the distal nail plate. They may, however, be beneficial in combination with oral drug therapy. In severe cases, the affected nail is removed surgically or by use of a urea-containing formulation, and the removal of the nail is done in conjunction with oral and sometimes with topical therapy.

Long-term systemic (oral) administration of an antifungal agent for the treatment of onychomycosis is currently required to produce a therapeutic effect. For example, oral treatment with the antifungal compound ketoconazole typically requires administration of 200 to 400 mg/day for at least 3-6 months. Such a long-term, high-dose systemic therapy can result in serious adverse effects. For example, ketoconazole has been reported to induce liver toxicity effects and reduces testosterone levels in the blood. Patient compliance is a problem with such long-term therapies, especially those with potentially serious adverse effects. In addition, azole antifungals are contraindicated and not recommended in patients with chronic hepatitis B virus (HBV). Chronic HBV affects about 20-30% of the Taiwanese population, which causes inconvenience in treatment of fungal toenail or fingernail infection.

Surgical removal of all or part of the nail followed by a topical treatment also has drawbacks. The pain and discomfort associated with the surgery and the undesirable cosmetic appearance of the nail or nail bed present significant problems, particularly for female patients or those concerned about physical appearance. Topical therapy has significant problems, too. Topical dosage forms such as cream, lotion gel, etc., do not keep the drug in intimate contact with the nail or foot for prolonged periods of time. Bandages have been used to hold drug reservoirs in place in an attempt to enhance absorption of the pharmaceutical agent. However, bandages are thick, awkward, and troublesome, and generally lead to poor patient compliance.

Hydrophilic and hydrophobic film-forming topical antifungal solutions have also been developed. These dosage forms provide improved contact between the drug and the nail, but the films are not occlusive. Topical formulations for onychomycosis treatment deliver the drug to the target site (an infected nail bed) only by diffusion across or through the nail. Human nail is more like hair than stratum corneum with respect to chemical composition and permeability. Nitrogen is the major component of the nail, reflecting the nail's proteinaceous nature. The total lipid content of a mature nail is 0.1-1.0% w/w, while the stratum corneum lipid is about 10% w/w. The nail is 100-200 times thicker than the stratum corneum and has a very high affinity and capacity for binding and retaining antifungal drugs. Consequently, little if any drug penetrates the nail to reach the target site. The same problem may also apply to a patch designed to be applied to the nail directly. U.S. Pat. No. 6,727,401 B1 discloses a pressure sensitive adhesive matrix patch for the treatment of onychomycosis wherein the matrix layer is adapted to be in diffusional nail contact with the infected nail and surrounding skin area. However, structural deformities and irregularities of infected nails usually impede transdermal drug delivery through the nail tissue. Delivery may be further hampered by poor contact between the patch and greater thickness of the nail. For these reasons, topical therapies for onychomycosis, including those utilizing patch devices, have generally been ineffective.

Onychomycosis is a localized fungal infection of the nail plate and nail bed. An ideal therapy for onychomycosis should maintain very high local tissue concentration of an antifungal agent in the nail and skin, and deliver effective drug amounts topically to the nail bed with minimum systemic exposure. A matrix patch device comprising an antifungal agent and configured for application to a dorsal site of an infected palm or foot, rather than over the infected nail and surrounding skin directly, would overcome all the disadvantages of conventional topical or systemic therapy for fungal infections.

There would therefore be benefit in providing a pressure-sensitive adhesive matrix patch device which not only enables passage of drug compositions into the skin tissues, and even the stratum corneum for tinea pedis to preclude additional invasive infection or prevent re-infection when used chronically, but also facilitates transdermal administration of an antifungal agent to treat fungal infections directly.

SUMMARY OF THE INVENTION

Accordingly, a primary objective of the present invention is to provide a pressure-sensitive adhesive matrix patch device of an antifungal agent for treatment or prevention of fungal nail or foot infections which can be applied to a dorsal site of an infected palm or foot without requiring direct application to an area of infection. The patch can deposit the antifungal agent within tissues close to the infected sites so as to treat the fungal nail or foot infection.

Another object of the present invention is to provide a method for the transdermal treatment or prevention of fungal nail or foot infections with an antifungal agent comprising adhesively securing to a dorsal site of an infected palm or foot a pressure-sensitive adhesive matrix patch device for a time sufficient to deliver an effective amount of the antifungal agent to an area of infection.

An additional object of the present invention is to limit the concentration of each antifungal agent in blood. Consequently, the patch contains multiple antifungal agents. Two major advantages of the present invention are that the combined antifungal agents can increase antifungal spectrum without increasing toxicity due to long-term use; and that, unlike systemic antifungal therapy, it is very suitable for long-term treatment or prevention, as is generally required for fungal nail or foot infections.

DETAILED DESCRIPTION

Figure 1:
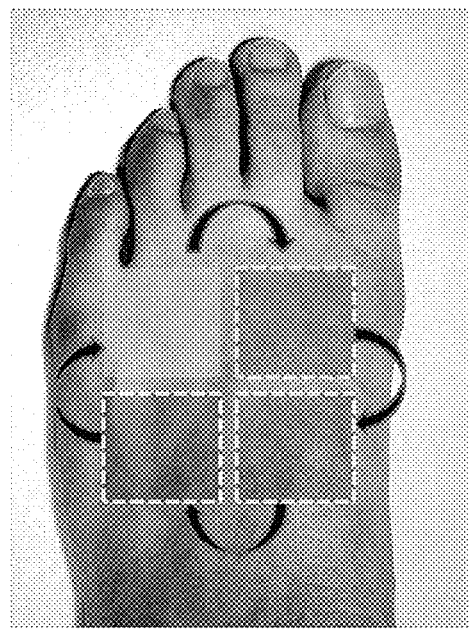
FIG. 1 shows the applied sites of the patch according to an embodiment of the present invention.

The above objects may be realized by means of a pressure-sensitive adhesive matrix patch device suitable for transdermal delivery of the antifungal agent. The pressure-sensitive adhesive matrix patch device for treatment or prevention of fungal nail or foot infections comprises:
 (a) an impermeable backing layer,
 (b) a matrix layer having a first surface and a second surface opposite the first surface, wherein the first surface is adhered to the backing layer and the second surface is adapted to be in diffusional skin contact with a dorsal site of an infected palm or foot, the matrix layer comprising:
  (i) a pressure-sensitive adhesive,
  (ii) an amount of an antifungal agent sufficient to provide an antifungal effect contained in the adhesive, wherein the antifungal agent comprises terbinafine or a pharmaceutically acceptable salt thereof, ketoconazole or a pharmaceutically acceptable salt thereof, or two or more above antifungals in combination, and
  (iii) a permeation enhancer; and
 (c) a release liner.

The present invention provides a method for transdermal treatment or prevention of fungal nail or foot infection with an antifungal agent, the method comprising adhesively securing to a dorsal site of an infected palm or foot a pressure-sensitive adhesive matrix patch device comprising:
 (a) an impermeable backing layer,
 (b) a matrix layer having a first surface and a second surface opposite the first surface, wherein the first surface is adhered to the backing layer and the second surface is adapted to be in diffusional skin contact with a dorsal site of an infected palm or foot, the matrix layer comprising:
  (i) a pressure-sensitive adhesive,
  (ii) an amount of an antifungal agent sufficient to provide an antifungal effect contained in the adhesive, wherein the antifungal agent comprises terbinafine or a pharmaceutically acceptable salt thereof, ketoconazole or a pharmaceutically acceptable salt thereof, or two or more above antifungals in combination, and
  (iii) a permeation enhancer; and
 (c) a release liner;
the device being adhesively secured to the dorsal site of the infected palm or foot for a time sufficient to deliver an effective amount of the antifungal agent to an area of infection.

According to the present invention, the transdermal patch and transdermal treatment method provide the minimum drug exposure to the body comparing to oral antifungal treatment.

According to the present invention, the antifungal agent is delivered through the skin, and most of those absorbed in the blood stream will be deposited quickly to epidermis (especially keratinocytes) of skin tissues and delivered to and deposited at the tissue of infected nails.

The following definitions, when used, will be helpful in describing the invention and will eliminate the need for repetitive explanation.

The term "matrix" means active skin permeation homogeneously combined in a biocompatible pressure-sensitive adhesive in which the enhancer is also homogeneously dissolved or suspended. A matrix system is usually an adhesive patch device having an impermeable backing layer and, before transdermal application, a release liner on the surface of the adhesive opposite the backing layer. A matrix system therefore is a unit dosage form of a drug composition in an adhesive carrier, also containing the enhancer and other components which are formulated for maintaining the drug composition in the adhesive in a drug transferring relationship with the skin.

According to the present invention, the fungal nail infections refer to fungal toenail or fingernail infections such as onychomycosis, and the fungal foot infections refers to tinea pedis.

The impermeable backing layer refers to a layer which regulates the access of liquid. The backing layer consists of a material which is permeable to water vapor but in itself is not water-soluble and is substantially impermeable to the antifungal agents to be delivered through transdermal permeation. A special mechanism for regulating the access of skin moisture is needed, because otherwise the active substance precipitates or the release of active substance is insufficient. Suitable impermeable backing layer is well known in the art. In an embodiment of the present invention, the impermeable backing layer is made from polyester, polyurethane, polyethylene, ethylene vinyl acetate (EVA), polyolefin, or other synthetic composition.

Suitable pressure-sensitive adhesives are well known in the art and may include, but are not limited to, acrylic adhesive, (e.g. National Starch Duro-tak® 2052, 2054, 2287, 2074, and 2677 and Monsanto Gelva® 737), rubber adhesive, such as poly-isobutylene or PIB adhesive, (e.g. Adhesive Research MA-24) and silicone adhesive" (e.g. Dow Bio-PSA). Preferably, the pressure-sensitive adhesive is an acrylic adhesive. However, any other suitable pressure-sensitive adhesives may also be used which are compatible with the antifungal agents and permeation enhancer when utilized.

According to the present invention, the antifungal agent comprises terbinafine or a pharmaceutically acceptable salt thereof, ketoconazole or a pharmaceutically acceptable salt thereof, or two or more above antifungals in combination.

Hydrochloride, sulfate, mesilate, citrate, fumarate, tartrate, maleate, acetate, or the like of terbinafine can be used as the pharmaceutically acceptable salt of terbinafine without particular limitations as long as the effects of the present invention are obtained. Terbinafine hydrochloride, which is the hydrochloride of terbinafine, is particularly preferably used.

According to the present invention, the terbinafine or pharmaceutically acceptable salt thereof is present in an amount of between about 1% to 20%, preferably about 1% to 15%, and more preferably about 1% to 10%, 1% to 8%, 1% to 5%, 2% to 10%, 2% to 8%, 2% to 5% or 5% to 10% by weight of the matrix layer.

Hydrochloride, sulfate, mesilate, citrate, fumarate, tartrate, maleate, acetate, or the like of ketoconazole can be used as the pharmaceutically acceptable salt of ketoconazole without particular limitations as long as the effects of the present invention are obtained. Ketoconazole hydrochloride, which is the hydrochloride of ketoconazole, is preferably used.

According to the present invention, the ketoconazole or pharmaceutically acceptable salt thereof is present in an amount of between about 1% to 20%, preferably about 1% to 10%, and more preferably about 1% to 5%, 1% to 8%, or 2% to 5% by weight of the matrix layer.

According to an embodiment of the present invention, the antifungal agent can be used in combination with other antifungal agents selected from the group consisting of miconazole, clotrimazole, econazole, bifonazole, butoconazole, fenticonazole, isoconazole, oxiconazole, sertaconazole, sulconazole, tioconazole, fluconazole, itraconazole, isavuconazole, ravuconazole, posaconazole, voriconazole, terconazole, abafungin, butenafine, tolnaftate, and griseofulvin.

Suitable permeation enhancers are well known in the art and may include, but are not limited to, fatty acids, fatty alcohol derivatives, aliphatic esters, aromatic esters, carboxylic acids, carboxylic esters, alcohols, polyol, triethylcitrate, triethylene glycol, diethylene glycol monoethyl ether, dodecyl-2-N,N-dimthylaminopropionate, diethylphthalate, oleic acid, propylene glycol, lauryl alcohol, ethyl acetate, laurylpyrrolidone, triethanolamine, glycerine, triacetine, diethyleneglycol monoethylether, triacetin, N-methyl-pyrrolidone, lauryl lactate, propylene glycol monolaurate, or diethyleneglycol monoethyl ether. Preferably, the permeation enhancer is selected from the group consisting of triacetin, N-methyl-pyrrolidone, lauryl lactate, propylene glycol monolaurate, and diethyleneglycol monoethyl ether.

According to the present invention, the permeation enhancer is present in an amount of between about 0.1% to 30%, preferably about 1% to 20%, and more preferably about 1% to 15%, 1% to 10%, 3% to 15%, 3% to 10%, 5% to 15% or 5% to 10% by weight of the matrix layer.

According to the present invention, a part of the adhesive is in contact with a release liner which seals and protects the adhesive during storage and which is capable of being peeled off and discarded prior to use of the matrix patch device. The release liner is released at the time of use of the patch and is not particularly limited. Suitable release liners are well known in the art and may include, but are not limited to, polymeric or paper origin. For example, polyethylene, polypropylene, or polyester subjected to release treatment is often used.

A method for producing the matrix patch device of the present invention is not particularly limited as long as it is a common method. One example thereof includes a method comprising: thermally melting a drug-containing matrix composition; coating a release liner or a backing layer with the solution; and bonding together the laminate and the backing layer or the release liner. Alternatively, the present agent can be obtained by: dissolving a drug-containing matrix component in a solvent such as toluene, hexane, or ethyl acetate; extending the solution on a release liner or a backing layer, followed by removal of the solvent by drying; and then bonding together the laminate and the backing layer or the release liner.

FIG. 1 shows the applied sites of the patch according to an embodiment of the present invention. As shown in FIG. 1, the patch can be applied to a first area of the dorsal site of the infected palm for a time sufficient to deliver an effective amount of the antifungal agent to an area of infection, and then the patch can be applied to a second, third, or fourth area; for example, along the arrows shown in FIG. 1; of the dorsal site of the infected palm, so that the antifungal agent can be uniformly deliver to the fungal infected toenails, and the skin of the infected palm will not have an allergic reaction due to the long-term use of the patch.

In an embodiment of the present invention, the patch is applied to the dorsal site of the infected palm or foot for at least two days, preferably at least three days, to deliver and deposit an effective amount of the antifungal agent to an area of infection.

The following examples are intended to further illustrate the present invention without limiting its scope. Modifications and variations that can be easily achieved by those skilled in the art are included in the scope of the disclosure of the specification and appended claims.

EXAMPLES

Example 1

Preparation of the Pressure-Sensitive Adhesive Matrix Patch Device of the Invention A pressure-sensitive adhesive matrix patch device comprising the compositions shown in Tables 1 and 2 below contained in a matrix layer was produced. Specifically, terbinafine, ketoconazole, and an enhancer listed in Tables 1 and 2 were well mixed. Then, the mixture was mixed with an adhesive dissolved in ethyl acetate. A release liner was coated with the solution, followed by removal of the ethyl acetate by drying. The laminate and a backing layer were bonded together to obtain the pressure-sensitive adhesive matrix patch device.

TABLE 1

|  | F-1 (wt %) | F-2 (wt %) | F-3 (wt %) | F-4 (wt %) | F-5 (wt %) |
| --- | --- | --- | --- | --- | --- |
| terbinafine | 2.5 | 2.5 | 2.5 | 2.5 | 2.5 |
| Duro-tak ® 2052 | 89.5 | 89.5 | 89.5 | 89.5 | 89.5 |
| triacetin | 8 | | | | |
| N-methyl-pyrrolidone | | 8 | | | |
| lauryl lactate | | | 8 | | |
| propylene glycol monolaurate | | | | 8 | |
| diethyleneglycol monoethyl ether | | | | | 8 |
| ethyl acetate | q.s. | q.s. | q.s. | q.s. | q.s. | q.s.: sufficient amounts

TABLE 2

|  | A (wt %) | B (wt %) | C (wt %) |
| --- | --- | --- | --- |
| terbinafine | 3 | 6 | 8 |
| ketoconazole | 2 | 2 | 2 |
| Gelva ® 737 | 87 | 84 | 82 |
| lauryl lactate | 8 | 8 | 8 |

TABLE 2-continued

|  | A (wt %) | B (wt %) | C (wt %) |
|---|---|---|---|
| ethyl acetate | q.s. | q.s. | q.s. | q.s.: sufficient amounts

Example 2

Skin Flux Methodology

1. Samples (1) Examples F-1, F-2, F-3, F-4, and F-5: 2.5 mg terbinafine/10 cm² patch (2) Lamisil cream (NOVARTIS®): 10 mg of terbinafine/g of cream (1%)

(3) Nizoral cream (JANSSEN-CILAG®): 20 mg of ketoconazole/g of cream (2%)

(4) Example A: 3 mg of terbinafine and 2 mg of ketoconazole/10 cm² patch (5) Example B: 6 mg of terbinafine and 2 mg of ketoconazole/10 cm² patch (6) Example C: 8 mg of terbinafine and 2 mg of ketoconazole/10 cm² patch 2. Testing Method and Steps (1) Skin penetration device Skin was cut into a predetermined area of several pieces, i.e., a width of about 10 mm and a length of about 42 mm. The skin pieces were immersed in water at 60° C. for about 75 sec. Then, the subcutaneous tissue and stratum corneum of the skin pieces were separated by a tweezer, and the stratum corneum was cut into a predetermined area of several pieces, i.e., 1 cm². The stratum corneum pieces were positioned at a side by side cell of skin penetration device, and controlled at 32° C. After peeling off the release liner of the matrix patch device, the matrix layer was adhesively secured to the stratum corneum pieces. A specially designed circular Teflon device covering an administration hole of the side by side cell is for the Lamisil cream and Nizoral cream. 20 mg Lamisil cream and 20 mg Nizoral cream were uniformly and separately applied on the device, and the device was adhesively adhered to the stratum corneum pieces. 3 ml of 10% PEG 400 was added into the cell as a medium. 0.5 ml of the medium was obtained and tested at appropriate times, and then the 0.5 ml medium was added into the cell.

(2) Sampling time: the 8th, 24th, 48th, and 72nd hour.

(3) Sample analysis: the samples were analyzed by using chromatography technique.

3. Results

Figure 2:
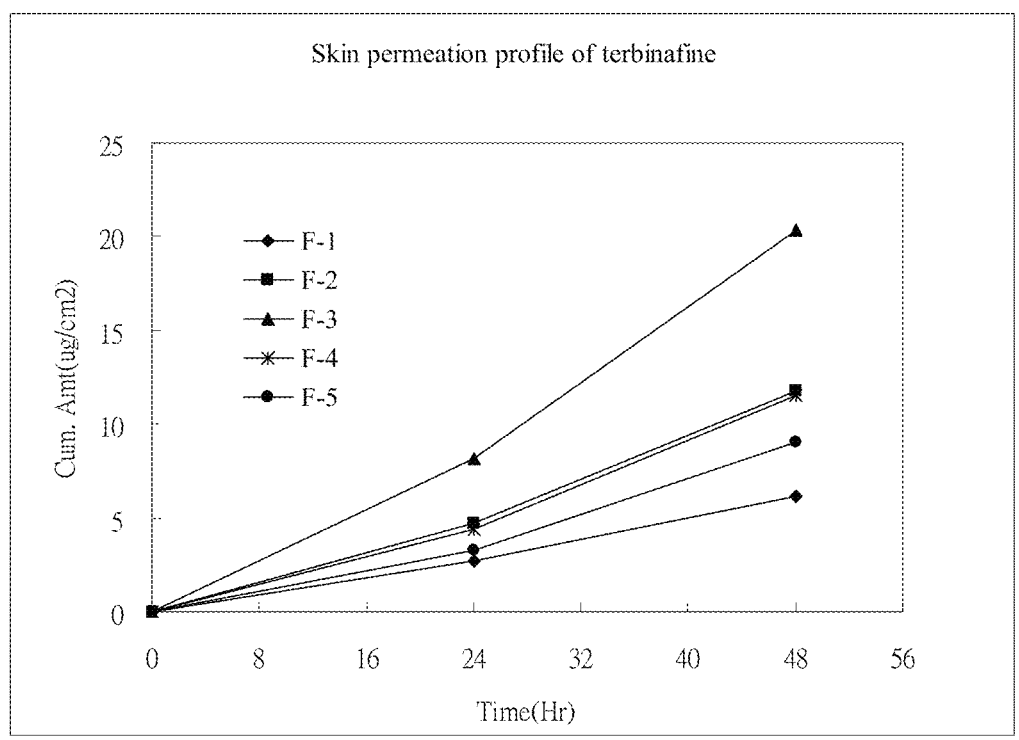
FIG. 2 shows the skin permeation profile of terbinafine used alone of Example 2.

FIG. 2 shows the skin permeation profile of terbinafine used alone. As shown in FIG. 2, the skin permeation amounts of Example F-3 are much higher than those of Examples F-1, F-2, F-4, and F-5.

Figure 3:
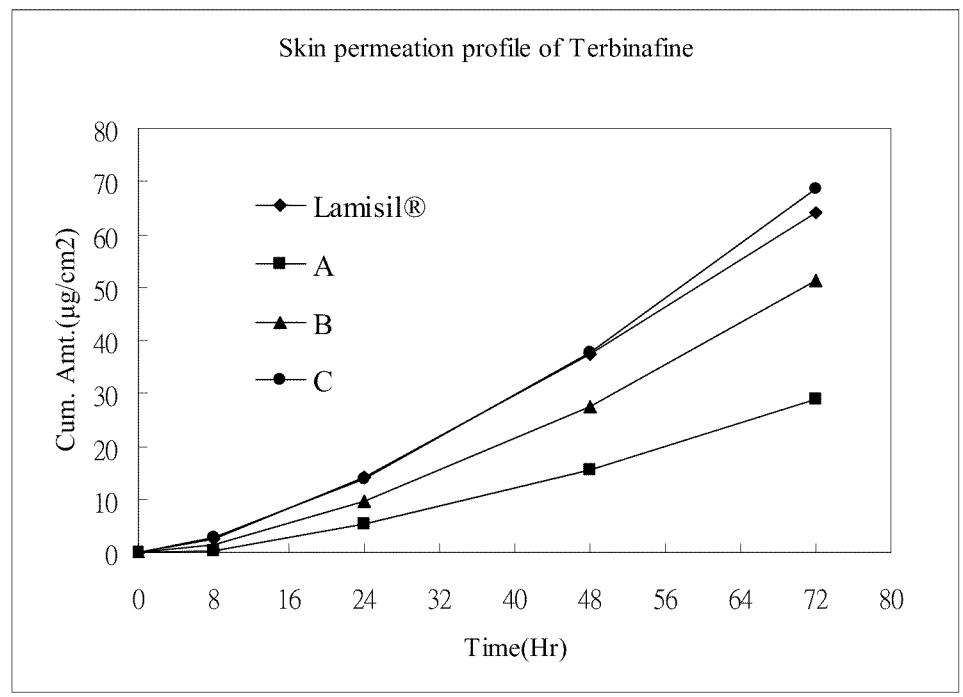
FIG. 3 shows the skin permeation profile of terbinafine in the combined antifungal agents of Example 2.
Figure 4:
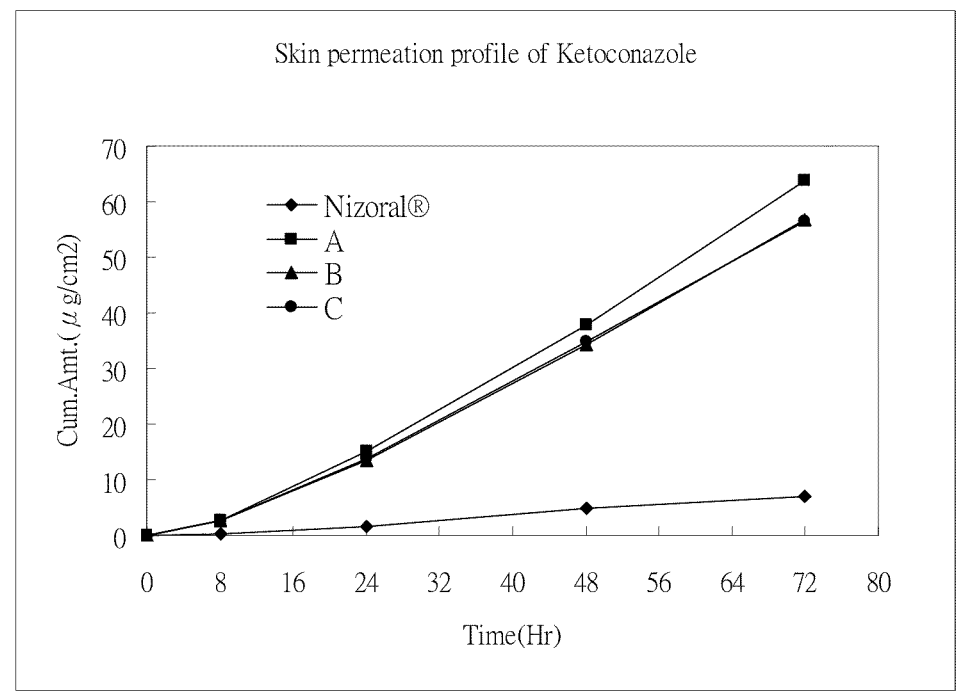
FIG. 4 shows the skin permeation profile of ketoconazole in the combined antifungal agents of Example 2.

FIG. 3 shows the skin permeation profile of terbinafine in the combined antifungal agents. FIG. 4 shows the skin permeation profile of ketoconazole in the combined antifungal agents. As shown in FIG. 3, the skin permeation profile of terbinafine in Example C is close to that of Lamisil cream, and the skin permeation profiles of Examples A to C are in proportion to the amounts of terbinafine. As shown in FIG. 4, the skin permeation amounts of Examples A to C (each of them comprises 2 mg of ketoconazole/10 cm² patch) are all higher than that of Nizoral cream (Nizoral cream comprises 20 mg of ketoconazole/g of cream). Moreover, since the amounts of ketoconazole in Examples A, B, and C are the same, their skin permeation profiles are similar to each other.

Given the above, the pressure-sensitive adhesive matrix patch device of the present invention, which is configured for application to a dorsal site of an infected palm or foot, rather than over the infected nail and surrounding skin directly, overcomes all the disadvantages of conventional topical or systemic therapy for fungal nail or foot infections. Moreover, the matrix patch device comprising combined antifungal agents can increase antifungal spectrum without increasing toxicity due to long-term use. Unlike systemic antifungal therapy, it is very suitable for long-term treatment or prevention, which is generally required for nail or foot infections.

It will be apparent to those skilled in the art that various modifications and variations can be made to the structure of the present invention without departing from the scope or spirit of the present invention. In view of the foregoing, it is intended that the present invention cover modifications and variations of this invention provided they fall within the scope of the following claims and their equivalents.

What is claimed is:

1. A pressure-sensitive adhesive matrix patch device for the treatment or prevention of fungal toenails or fingernails or foot infections comprising:

(a) an impermeable backing layer, (b) a matrix layer having a first surface and a second surface opposite the first surface, wherein the first surface is adhered to the backing layer and the second surface is adapted to be in diffusional skin contact with a dorsal site of an infected palm or foot, the matrix layer comprising:

(i) a pressure-sensitive adhesive, wherein the pressure-sensitive adhesive is an acrylic adhesive;

(ii) an amount of an antifungal agent sufficient to provide an antifungal effect contained in the adhesive, wherein the antifungal agent is selected from 2% to 8 % by weight of terbinafine and a combination of 2% to 8% by weight of terbinafine and 1% to 5% by weight of ketoconazole, based on weight of the matix layer; and (iii) 5% to 10% by weight of a permeation enhancer based on the weight of the matrix layer, wherein the permeation enhancer is lauryl lactate; and (c) a release liner; the device being adhesively secured to the dorsal side of the infected palm or foot for a time sufficient to deliver an effective amount of the antifungal agent to an area of infection.

2. The device according to claim 1, wherein the fungal toenails or fingernails or foot infections are selected from the group consisting of *onychomycosis* and *tinea pedis*.

3. The device according to claim 1, wherein the impermeable backing layer is made from polyester, polyurethane, polyethylene, ethylene vinyl acetate (EVA), polyolefin or the mixtures thereof.

4. The device according to claim 1, wherein the terbinafine or pharmaceutically acceptable salt thereof is present in an amount of between about 2% to 5%, or 5% to 8% by weight of the matrix layer.

5. The device according to claim 1, wherein the ketoconazole or pharmaceutically acceptable salt thereof is present in an amount of between about 2% to 5% by weight of the matrix layer.

6. The device according to claim 1, wherein the antifungal agent can be used in combination with other, antifungal agents selected from the group consisting of miconazole, clotrimazole, econazole, bifonazole, butoconazole, fenticonazole, isoconazole, oxiconazole, sertaconaloze, sulconazole, tioconazole, fluconazole, itraconazole, isavuconazole, ravuconazole, posaconazole, voriconazole, terconazole, abafungin, butenafine, tolnaftate, and griseofulvin.

7. A method for the transdermal treatment of fungal toenails or fingernails or foot infections with an antifungal agent comprising adhesively securing to a dorsal side of an infected palm or foot a pressure-sensitive adhesive matrix patch device comprising:

(a) an impermeable backing layer, (b) a matrix layer having a first surface and a second surface opposite the first surface, wherein the first surface is adhered to the backing layer and the second surface is adapted to be in diffusional skin contact with a dorsal side of an infected palm or foot, the matrix layer comprising:

(i) a pressure-sensitive adhesive, wherein the pressure-sensitive adhesive is an acrylic adhesive;

(ii) an amount of an antifungal agent sufficient to provide an antifungal effect contained in the adhesive, wherein the antifungal agent is selected from 2% to 8% by weight of terbinafine and a combination of 2% to 8% by weight of terbinafine and 1% to 5% by weight of ketoconazole, based on weight of the matrix layer; and (iii) 5% to 10% by weight of a permeation enhancer based on the weight of the matrix layer, wherein the permeation enhancer is lauryl lactate; and (c) a release liner;

the device being adhesively secured to the dorsal side of the infected palm or foot for a time sufficient to deliver an effective amount of the antifungal agent to an area of infection.

8. The method according to claim 7, wherein the fungal toenails or fingernails or foot infections are selected from the group consisting of *onychomycosis* and *tinea pedis*.

9. The method according to claim 7, wherein the impermeable backing layer is made from polyester, polyurethane, polyethylene, ethylene vinyl acetate (EVA), polyolefin or the mixtures thereof.

10. The method according to claim 7, wherein the terbinafine or pharmaceutically acceptable salt thereof is present in an amount of between about 2% to 5%, or 5% to 8% by weight of the matrix layer.

11. The method according to claim 7, wherein the ketoconazole or pharmaceutically acceptable salt thereof is present in an amount of between about 2% to 5% by weight of the matrix layer.

12. The method according to claim 7, wherein the antifungal agent can be used in combination with other antifungal agents selected from the group consisting of miconazole, clotrimazole, econazole, bifonazole, butoconazole, fenticonazole, isoconazole, oxiconazole, sertaconaloze, sulconazole, tioconazole, fluconazole, itraconazole, isavuconazole, ravuconazole, posaconazole, voriconazole, terconazole, abafungin, butenafine, tolnaftate, and griseofulvin.

* * * * *